United States Patent [19]

Pascone

[11] Patent Number: 4,713,480
[45] Date of Patent: Dec. 15, 1987

[54] METHOD FOR THE PRODUCTION OF CRYSTALLINE AMINO-PROTECTED-BETA-BENZYL-L-ASPARTIC ACID

[75] Inventor: John M. Pascone, Neshanic Station, N.J.

[73] Assignee: Ortho Pharmaceutical Corporation, Raritan, N.J.

[21] Appl. No.: 1,076

[22] Filed: Jan. 7, 1987

[51] Int. Cl.$^4$ .......................................... C07C 125/065
[52] U.S. Cl. ....................................... 560/157; 560/163
[58] Field of Search .................................. 560/163, 157

[56] References Cited

U.S. PATENT DOCUMENTS

| | | | |
|---|---|---|---|
| 3,062,804 | 11/1962 | Albertson | 560/24 |
| 3,062,805 | 11/1962 | Albertson | 560/32 |
| 3,445,447 | 5/1969 | Sakakibara | 560/157 |
| 3,609,164 | 9/1971 | Nishinomiya | 560/157 |
| 3,711,458 | 1/1973 | Olofson | 560/157 |
| 3,775,466 | 11/1973 | Jager | 560/163 |
| 3,875,207 | 4/1975 | Iselin | 560/163 |
| 3,891,692 | 6/1975 | Ueber | 560/163 |
| 3,906,031 | 9/1975 | Carpino | 560/32 |
| 4,082,736 | 4/1978 | Jones | 260/112.5 |
| 4,440,692 | 4/1984 | Kalbacher | 560/162 |

Primary Examiner—Michael L. Shippen
Attorney, Agent, or Firm—Geoffrey G. Dellenbaugh

[57] ABSTRACT

An amino-protected L-aspartic acid, such as t-butyloxycarbonyl-beta-benzyl-L-aspartic acid, is prepared by first forming the amino-protected compound in the presence of a tertiary amine base having a p$K_a$ value of about 9 to about 12, water, and a water-immiscible polar organic solvent so as to produce a non-aqueous solution containing a salt form of amino-blocked-beta-benzyl-L-aspartic acid. The thus produced non-aqueous solution is then isolated, or next acidified and treated further to ultimately recover therefrom the amino-protected L-aspartic acid in crystalline form.

13 Claims, No Drawings

METHOD FOR THE PRODUCTION OF CRYSTALLINE AMINO-PROTECTED-BETA-BENZYL-L-ASPARTIC ACID

TECHNICAL FIELD

This invention relates to amino-protected amino acids in crystalline form, and, in particular, to a method for obtaining such acids in high yields. More particularly, this invention relates to a method of preparing crystalline, amino-blocked beta-benzyl-L-aspartic acid, and particularly t-butyloxycarbonyl-beta-benzyl-L-aspartic acid, in high yield.

BACKGROUND ART

Protected amino acids, that is, amino acids having the amine functional group thereof blocked by an amino-protective group, are sometimes called N-blocked amino acids. These protected amino acids are widely used in the field of biochemistry. Commercially, amino-protected amino acids are useful as starting materials for the synthesis of polypeptides and proteins. These synthetic polypeptides and proteins have important application in the fields of medicine, industry, pharmacology and most especially immunology.

L-aspartic acid derivatives are particularly useful in the synthesis of biologically-active polypeptides as disclosed in U.S. Pat. No. 4,298,523 to Heavner, pertinent portions of which are incorporated herein by reference.

Peptide syntheses are hampered by low yields of relatively pure product when synthesis is attempted without first preventing undesired reactions of the amine portion of the molecule. Undesired reactions are prevented by attaching a protective group to the amine portion of the molecule, wherein the amino-protective group is unreactive in the subject reaction, but where the amino-protective group is later readily removable from the protected amino acid without causing destruction of the desired synthesis product. Tertiary butyloxycarbonyl (BOC) is a well-known protective group, and the use of BOC-protected amino acids is widely known in the art.

A frequently encountered difficulty in peptide synthesis, particularly of long chain polypeptide synthesis, is in obtaining the long chain polypeptides in relatively high yields. It is well known that unless each of the reactions in the step-wise long chain polypeptide synthesis can be made nearly quantitative, the yield of product that can be prepared from starting materials in economic amounts will be exceedingly small. The use of amino-protective groups, on the other hand, prevents the undesirable side reactions that reduce the yield of a desired polypeptide in step-wise peptide synthesis.

It is further desirable, particularly in the syntheses of biologically active peptides, that the amino-protected amino acid used be in a relatively pure, more preferably crystalline form. The relatively pure, amino-protected amino acid, as a solution or crystalline, prevents undesirable contamination of the peptide synthesis reaction with reaction products of the amino-protected amino acid, and thus allows peptide synthesis to proceed using a reasonable amount of the amino-protected amino acid in the reaction.

Crystalline tert-butyloxycarbonyl-beta-benzyl-L-aspartic acid is commercially available, for example, from Bachem Biochemicals, Torrance, Calif., Peninsula Laboratories, Inc., Belmont, Calif., as well as from other sources. The compound is relatively expensive, however.

Thus, there is a need for relatively high purity amino-protected beta-benzyl-L-aspartic acid that is relatively easy to obtain in relatively high yields and readily usable in the synthesis of biologically important compounds.

SUMMARY OF THE INVENTION

This invention provides a method of preparing amino-protected amino acids in crystalline form or in a solution in relatively pure form. In one aspect, the present invention provides a method for obtaining relatively high purity, crystalline, amino-protected beta-benzyl-L-aspartic acid in a relatively high yield. In a preferred aspect of this invention, crystalline t-butyloxcarbonyl-beta-benzyl-L-aspartic acid having a melting point of about 100.5° C. to about 102.5° C. is prepared. This material has a purity of at least about 95 percent, usually about 97.5 percent or higher.

The method of this invention contemplates combining an oxycarbonyl compound that provides an amino protecting group with beta-benzyl-L-aspartic acid and with a tertiary amine organic base in the presence of water and a water-immiscible polar organic solvent so as to produce a non-aqueous solution of a salt of the amino-blocked beta-benzyl-L-aspartic acid. The tertiary amine organic base has a $pK_a$ value of about 9 to about 12, and preferably is triethylamine. The produced reaction admixture is basic, having a pH value of about 7.5 to about 9, preferably about 8 to about 8.5. The thus-produced non-aqueous solution of a salt of the amino-blocked beta-benzyl-L-aspartic acid is recovered and water as well as a water-insoluble, non-polar organic liquid phase modifier are added thereto to produce a liquid having an aqueous phase and an organic liquid phase. The produced liquid is then acidified to a pH value of about 0.5 to about 2, the organic liquid phase is separated from the acidified liquid, and an additional amount of the organic liquid phase modifier is added to the separated organic liquid phase sufficient to induce crystallization of amino-blocked beta-benzyl-L-aspartic acid from the separated organic liquid phase. Preferably, the aforementioned additional amount of the organic liquid phase modifier is added stage-wise during the crystallization of the amino-blocked beta-benzyl-L-aspartic acid. If desired, the aforesaid non-aqueous solution can be recovered before acidification and used directly for peptide synthesis.

In a preferred embodiment, a t-butyloxycarbonyl protective group-providing reactant such as di-t-butyl-dicarbonate is reacted, in a system containing a polar organic liquid and water, with a triethylamine salt of beta-benzyl-L-aspartic acid. An organic phase and an aqueous phase of the reaction products are obtained.

The organic phase is then acidified, a $C_5$ to $C_8$ liquid aliphatic hydrocarbon is added stage-wise as the phase modifier to promote crystallization, and crystalline t-butyloxycarbonyl-beta-benzyl-L-aspartic acid is recovered therefrom.

The crystalline L-aspartic acid derivative produced in accordance with the present invention is useful for the production of chemically synthesized polypeptide derivatives as described, for example, in the aforementioned U.S. Pat. No. 4,298,523 to Heavner, in U.S. Pat. No. 4,190,646 to Goldstein and Schlesinger and in U.S.

Pat. No. 4,392,997 to Goldberg, the pertinent disclosures of which are incorporated herein by reference.

As a further example, the crystalline amino-protected L-aspartic acid derivative prepared by the method of this invention is useful for the so-called "solid phase" peptide synthesis involved in the stepwise addition of amino-protected amino acids to form or add to a peptide chain, especially by the method of Merrifield et al. as reported, for example, in Science 150: 178-185 (1965). These derivatives are also useful for preparing polypeptides by classical techniques as taught in, for example, M. Bodanszky, et al., *Peptide Synthesis,* Olah, ed., Interscience, John Wiley & Sons, Inc., N.Y., N.Y., 2d Ed. (1976).

An advantage of the method of this invention is that a yield in excess of 90 percent of theoretically calculated amount of crystalline amine protected beta-benzyl-L-aspartic acid can be readily harvested. These crystals are substantially free of organic base salts of the amino acid.

Still further benefits and advantages of the present invention will be apparent to those skilled in the art from the detailed description and examples that follow.

DETAILED DESCRIPTION OF PREFERRED EMBODIMENTS

Crystalline amino-protected beta-benzyl-L-aspartic acid having its amino functional group blocked with an amino-protective group can be prepared by the method of this invention without losing a substantial amount of the protective groups. Furthermore, the produced crystalline amino-protected L-aspartic acid is substantially free of organic salt contaminants.

A number of methods are known in the art for reacting beta-benzyl-L-aspartic acid with an amino-protective-group adding reagent for purposes of blocking the amino-functional group so as to protect it from unwanted peptide bond reactive reagents until a later desired peptide bond reaction is accomplished. However, recovery of relatively pure amino-protected beta-benzyl-L-aspartic acid from the resulting admixture of reactants and reaction products is difficult.

The reagents employed to introduce amino protecting groups are sometimes referred to herein as "amino-protective-group adding reagents." A discussion of these reagents and suitable protective groups can be found in, for example, *Protective Groups in Organic Chemistry,* J. F. W. McOmie, ed., Plenum Press, N.Y., N.Y., (1983), and in the *Concise Encyclopedia of Biochemistry,* Walter de Gruyter, N.Y., N.Y. (1983) the pertinent portions of which are incorporated herein by reference.

Typically, the amine group of unprotected beta-benzyl-L-aspartic acid can be protected or blocked by reacting it with a compound containing an amino protective group, for example, an oxycarbonyl compound which includes the structure having the formula R—O—CO—, wherein R is any moiety that will prevent the amino group from entering into subsequent coupling reactions and that can be removed without concurrent destruction of the L-aspartic acid-containing molecule.

Thus, R can be a straight or branched chain $C_1$ to $C_{10}$ alkyl group which may be saturated or unsaturated; a $C_6$ to $C_{15}$ aryl group; a $C_5$ to $C_8$ cycloalkyl group; a $C_7$ to $C_{18}$ aralkyl group; a $C_7$ to $C_{18}$ aralkyl group or a heterocyclic group, e.g., isonicotinyl.

Preferred groupings for R include tert-butyl, tert-amyl, tolyl, xylyl and benzyl. Highly preferred specific amino-protecting groups include tert-butyloxycarbonyl, benzyloxycarbonyl, substituted by one or more halogens, e.g., Cl or Br, nitro, $C_1$ to $C_4$ alkoxy, e.g., methoxy, or $C_1$ to $C_4$ alkyl substituents; tert-amyloxycarbonyl; cyclohexyloxycarbonyl; vinyloxycarbonyl; adamantyloxycarbonyl; 2-(p-biphenylyl)isopropoxycarbonyl; and the like. Other amino-protecting groups which can be used include isonicotinyloxycarbonyl, phthaloyl, p-tolylsulfonyl, formyl and the like.

As used herein, the term "halo" includes fluoro, chloro, bromo, and iodo, but chloro and bromo are preferred. The terms "lower alkyl" and "lower alkoxy" include, respectively, saturated aliphatic $C_1$ to $C_6$ hydrocarbons, such as methyl, ethyl, isopropyl, tert-butyl, n-hexyl, and the like, and the corresponding alkoxy groups, such as methoxy, ethoxy, isopropoxy, tert-butoxy, n-hexoxy, and the like.

The tertiary amine base used to make an organic base salt of beta-benzyl-L-aspartic acid in accordance with the present invention is preferably one having a $pK_a$ value of about 9 to about 12, and most preferably is triethylamine ($pK_a$ 10.65). Other suitable tertiary amines include those containing three lower alkyl ($C_1$–$C_6$) groups on an amino-nitrogen atom, such as trimethylamine ($pK_a$ 9.76), tri-n-propylamine ($pK_a$ 10.65), diisopropylethylamine ($pK_a$ 10.5), tri-n-butylamine ($pK_a$ 10.89), methyldiethylamine ($pK_a$ 10.29) or the like; and heterocyclic tertiary amines, such as N-methylpiperidine ($pK_a$ 10.08), N-ethylpiperidine ($pK_a$ 10.40), 4-dimethylaminopyridine ($pK_a$ 9.7), or the like. The tertiary amine is a hindered, non-nucleophilic base which, therefore, does not hydrolyze the benzyl ester.

The reaction mixture is kept basic, preferably at a pH value of about 8 to about 8.5, and as a result a salt is also formed with the carbonic acid generated from the carbon dioxide and water that are present in the reaction mixture. If the reaction mixture were not kept basic, the carbonic acid present would form a salt with the amino group on the beta-benzyl-L-aspartic acid and the desired reaction would stop.

Inorganic bases are not satisfactory substitutes for tertiary amines as salt formers with beta-benzyl-L-aspartic acid. For example, if sodium hydroxide is used as the base, its strong alkalinity promotes hydrolysis at the benzyl ester site and produces t-butyloxycarbonyl-L-aspartic acid as a by product. On the other hand, when a weak inorganic base, such as magnesium oxide, is used as the salt former, the addition of the tertiary butyloxycarbony radical, or other suitable amino protective group, does not go to completion.

Similarly, the reaction does not go to completion when a weak organic base such as N-methylmorpholine ($pK_a$ 7.41) is used as the salt former.

To prepare a substantially pure, crystalline amino-blocked beta-benzyl-L-aspartic acid in a high yield, a non-aqueous solution containing the amino-blocked compound in salt form is isolated and subjected to crystallization and, optionally, to further purification.

In practicing one aspect of the present method, initially a non-aqueous solution of a salt of an amino-blocked L-aspartic acid is prepared in a substantially water-immiscible polar organic solvent for the L-aspartic acid derivative in a system which also includes a separate aqueous phase. The resulting amino salt solution can be used for peptide synthesis directly, if desired. Alternatively, if a crystalline form of the amino-blocked L-aspartic acid is desired, the polar organic solvent solution is combined, prior to the crystallization step, with a non-polar organic liquid phase modifier which is immiscible with water but is miscible with the water-immiscible polar solvent. While the phase modifier is not a solvent for the L-aspartic acid derivative, it decreases the solubility of the L-aspartic acid derivative in the polar solvent. The preferred organic liquid non-polar phase modifier is a liquid aliphatic $C_5$ to $C_8$ hydrocarbon, such as n-pentane, n-hexane, n-heptane, isooctane, and mixtures thereof. A particularly preferred phase modifier is n-heptane.

The phase modifier usually is added stage-wise. That is, about 1 to 2 parts by weight of the phase modifier per part by weight of the theoretical end product are added to the produced mixture of reactants and reaction products prior to acidification, another 4 to 5 parts/part are added prior to crystallization, followed by about 3 to 3.5 parts/part after crystallization has commenced. Finally, about 2 parts by weight of the phase modifier per part by weight of theoretical end product are added after the polar organic solvent has been distilled off to further maximize the crystal yield.

A nucleating agent is preferably used to initiate crystallization. Techniques for seeding are well-known in the art. A suitable nucleating agent is a seed crystal of the same amino protected L-aspartic acid or an inert nucleation promoter, such as powdered glass, glass stirrers, and the like.

A nucleating seed crystal can be obtained, if desired, by the crystallizing method as described hereinbelow in Example 1, or from a commercial source.

In practicing the method of this invention crystallization can be carried out at temperatures substantially above room temperature. However, higher yields are more reproducibly obtained at temperatures in the range of about 18° C. to about 35° C., preferably about 20° C. to about 25° C.

Suitable polar organic solvents include $C_1$ to $C_2$ alkyl halides, such as chlorinated methanes and chlorinated ethanes. Suitable chlorinated methanes include methylene chloride, chloroform and carbon tetrachloride. Suitable chlorinated ethanes include perchloroethylene, 1,1,2,2-tetrachloro-ethane, and the like. Methylene chloride and chloroform are particularly preferred.

To form an illustrative reaction mixture, preferably first methylene chloride, di-t-butyldicarbonate, beta-benzyl-L-aspartic acid and water are placed into a reaction vessel. Triethylamine and methylene chloride, in a volumetric ratio of about 1:1, are added to the reaction vessel slowly at a temperature of about 3° C. to about 40° C. and at a rate sufficient to maintain the resulting reaction mixture at a pH value of about 8 to about 8.5.

The triethylamine-methylene chloride solution preferably is freshly prepared. In any event, it should not be stored for more than 24 hours because extended storage results in undesirable reaction products of triethylamine and methylene chloride.

It has been found that when the temperature of the reaction mixture during the triethylamine and methylene chloride addition was maintained at about 30° C. to about 35° C., about 1.5 to about 2 hours were required for completion of the reaction. Completion is determined by the absence of solid material in either the aqueous or the organic layer, and may be confirmed by thin layer chromotography on silica gel G-plates, or GF-plates eluted with chloroform, methanol, acetic acid in a respective ratio of 70:25:5, followed by visualization with ninhydrin and heat. The organic layer or phase contains the desired reaction product which is subsequently recovered therefrom.

The reaction pH is controlled to avoid protonation of the amino group, which would lead to an incomplete reaction. Only one t-butyldicarbonate group of the di-t-butyldicarbonate reacts with the amino group. The rest of the molecule decomposes to t-butyl alcohol and carbon dioxide. The latter reacts with the water present to form carbonic acid. Therefore, as the reaction proceeds, the pH drops. Although too high a pH will cause difficulties by di-t-butyldicarbonate decomposition and benzyl ester hydrolysis during the reaction, the pH value must be basic, e.g., about 7.5 to about 9 to avoid the incomplete reactions that have been found to occur at pH values of about 7 and below.

It has also been found that once the BOC-substituted amino acid is present in the organic layer, it is less susceptible to hydrolysis. Any hydrolysis that does occur, either before or after product formation, gives compounds that remain in the aqueous layer. Thus, using methylene chloride as the organic solvent and triethylamine-methylene chloride as the organic base solution to maintain a pH value of about 8 to about 8.5 at 40° C. to 45° C., the reaction goes to completion readily. The majority of the BOC-beta-benzyl-L-aspartic is dissolved in the organic layer, free from both L-aspartic acid and BOC-L-aspartic acid. No BOC-L-aspartic acid formation has been seen in either phase, although some hydrolysis has been confirmed by the presence of L-aspartic acid in the aqueous layer.

When ethyl acetate was substituted for methylene chloride as the polar organic solvent, the reaction went to completion, but some BOC-L-aspartic acid was observed in both the aqueous layer and in the organic layer. After acidification this could contaminate the desired product, thus methylene choride is the preferred polar organic solvent.

While the reaction can be effected at room temperature, it has been found desirable to initiate the reaction at an elevated temperature, so as to hasten the completion thereof. The reaction temperature is preferably between about 30° C. and about 40° C. With methylene chloride as the polar organic solvent, it is most preferable to maintain the temperature at about 30° C. to about 35° C. so as to minimize foaming in the reaction vessel.

The reaction time is significantly shorter at temperatures above ambient. After the initial heating, the desired temperature range is maintained throughout the reaction by cooling and/or controlling the exotherm by adjusting the rate of addition of the organic base.

Foaming of the reaction mixture can be controlled by maintaining the specified temperatures and pH ranges, and by adjusting the rate of triethylamine-methylene chloride addition, or adjusting the rate of triethylamine addition alone. The most likely cause of foaming is believed to be carbon dioxide evolution with ensuing vaporization of methylene chloride. Foaming may also be controlled by the addition of an anti-foaming agent such as simethicone NF [Dow Corning Medical Antifoam A. (Dow Corning, Midland, Mich.)]. Finally, foaming may also be controlled by adjusting the pH downwardly to a value of about 7.8 to about 8.5.

After the reaction is completed, the organic phase is recovered and water as well as the organic liquid phase modifier are added thereto. Acidification of the organic phase is then undertaken to convert completely the triethylamine salt of BOC-benzyl-L-aspartic acid to free BOC-benzyl-L-aspartic acid without removing the BOC group. The free BOC-beta-benzyl-L-aspartic acid remains in the organic layer during this procedure. Triethylamine salt in the final crystalline product at levels greater than 0.3 percent is considered to be a contaminant. The amount of triethylamine salt present in the crystalline BOC-beta-benzyl-L-aspartic acid is controlled by the addition of the acid during the acidification step.

The main consideration in choosing the acid is that it be strong enough to convert the triethylamine salt of the product to the corresponding free acid form using a reasonable amount of acid. Aqueous solubility of the acid is desirable so that excess acid remains in the aqueous layer. Mineral acids are preferred. A 6 N aqueous solution of HCl has been found to be suitable.

Acidification with citric acid may also be accomplished. However, excess citric acid along with sodium citrate tends to saturate the aqueous layer, thereby minimizing the acidified product solubility in the aqueous layer and ultimately preventing the conversion of the salt of BOC-beta-benzyl-L-aspartic acid to the relatively pure free acid form.

Only about 1.2 to 1.4 equivalents of hydrochloric acid have been found to be necessary to achieve the pH of 1.5 plus or minus 0.2, whereas about 4 to 5 equivalents of citric acid were needed for the same result.

The use of hydrochloric acid requires external cooling as the reaction is exothermic. Accordingly, preferably acidification is effected at a temperature below ambient temperature to minimize the possibility of BOC group removal under acidic conditions.

Organic acids other than citric acid may also be used, but the results are less satisfactory. Complete conversion of the triethylamine salt of BOC-beta-benzyl-L-aspartic acid to the corresponding free acid was not obtained with either formic acid or with p-toluene-sulfonic acid.

Results obtained with 6 N HCl were consistent in giving high yields of substantially pure final product. The triethylamine salt content using the n-heptane addition in the isolation step was below 0.3 percent.

Stirring during acidification and a contact time between about 1 and about 2 hours help the acidification to go to completion.

After acidification, the layers are separated; the organic layer is washed with water and then separated once more. Thereafter, the organic layer is heated to reflux temperature (40° C.–55° C. when the polar solvent is methylene chloride) and some of the liquid phase modifier (e.g., n-heptane) is added.

The volume of the organic layer may be adjusted for optimum crystallization conditions by dilution with additional polar solvent (for greater volume) or by distillation (for lesser volume).

A small amount of crystals of the desired product is then added for seeding. Additional liquid phase modifier is also added, slowly and with stirring, as crystallization begins at a temperature of about 30° C. to about 35° C.

The resulting mixture may then be distilled under vacuum to drive off more of the polar solvent, and more of the phase modifier can be added to increase crystal yield.

After cooling and additional stirring, the mixture is filtered to recover the crystals. The obtained filter cake is washed with fresh phase modifier.

Yields in the range of about 87 to about 95 percent are obtained when the total solvent concentration is between 10 to about 10.5 parts of solvent per gram of product using either ethyl acetate or methylene chloride as the polar solvent. The n-heptane ratio to ethyl acetate or methylene chloride preferably is in the range of about 4:1 to about 5:1.

Seeding of the product solution with previously obtained BOC-beta-benzyl-L-aspartic acid (e.g., from performing the steps of Example 1) has been a successful means of commencing crystallization. Seeding has been best at a temperature of about 30° C. to 35° C. A higher temperature at seeding tends to dissolve the seed crystals while lower temperatures such as room temperature result in an undesirably rapid rate of crystallization.

Distillation under reduced pressure, typically at 30° C. to 40° C. and 15 to 25 inches mercury (Hg), does not adversely affect the solubility of the product or the fluidity of the mixture but is useful in removing the polar solvent. This distillation is done after the initial crystallization. Distillation is carried out until the volume is about 10 to about 11 milliliters per gram of theoretical product.

During atmospheric distillation, the precipitated product begins to dissolve at about 40° C. to 45° C. and is completely dissolved at about 60° C. In such a case, heavy, rapid precipitation occurs during subsequent cooling to room temperature. Distillation under reduced pressure is preferred, however, for better quality crystals.

Without addition of n-heptane after distillation, yields of product are in the 73 to 77 percent range. This yield is increased significantly by adding n-heptane to the mixture after distillation. This addition takes place at about 30° C. to 35° C. to avoid too rapid precipitation from cooling, but can be done at room temperature without adverse effect. The total amount of n-heptane added to the solution is preferably about 10 to about 15 parts of n-heptane per part of methylene chloride. In one run, utilizing about 11.9 parts of n-heptane per part of methylene chloride, a yield of 94.5 percent was obtained.

In the filtration step, the mixture may be stirred for a time period of about two hours to about 18 hours before filtration without affecting the yield. In addition, the product may be washed after filtration, as is described in Example 1 hereinbelow. n-Heptane at room temperature does not appear to have an adverse effect on the yield or the quality of the product.

EXAMPLE 1: Production of
BOC-Beta-Benzyl-L-Aspartic Acid

A 5-liter jacketed, round bottom reaction vessel, fitted with a mechnical stirrer, pH meter electrode, thermometer, condenser and pressure equalizing addition funnel was charged with methylene chloride (769 ml) followed by the addition of di-t-butyldicarbonate (635.13 g; 2.82 moles, MW 218.25) while stirring. The temperature dropped from 20° C. to 7° C. due to the addition of cold di-t-butyldicarbonate or endotherm. The solution was clear and colorless.

Water (1281 ml) was then added to the reaction vessel followed by the slow addition of beta-benzyl-L-aspartic acid (571.81 g; 2.56 moles). The beta-benzyl-L-aspartic acid was added slowly to ensure adequate mixing of the resulting three phase mixture. The three phase mixture had a pH value of about 3.4 to about 3.7 at 19°–20° C. as measured with a pH meter standardized with buffer having a pH value of 7.0 at 25° C.

A solution of equal volume portions (512 ml each) of triethylamine (3.67 moles) and methylene chloride was prepared. This solution was added to the three phase mixture in 15 to 20 ml portions. During this addition, the pH value of the three-phase mixture was maintained in the desired range of about 8.0 to about 8.5 by adjusting the rate of addition. The obtained mixture was then heated to a temperature of about 30° C. to about 40° C.

During heating, more of the triethylaminemethylene chloride solution was slowly added so as to maintain the pH value in the range of 8.0 to about 8.5. The rate at which triethylamine-methylene chloride was added was increased as the reaction progressed but was adjusted downwardly to control an exotherm that caused undesirable foaming to occur at about 38° C. to about 40° C. Upon completing the addition of the triethylamine-methylene chloride solution, the mixture was stirred for about one hour. During this time the temperature was maintained at about 30° C. to about 35° C. No solids were observed to be present in the reaction vessel at the end of the stir period.

Extraction of the BOC-beta-benzyl-L-aspartic acid was then commenced. The aqueous and organic layers were separated according to standard methods. Any organic component remaining in the aqueous layer was extracted with methylene chloride (641 ml). The methylene chloride extraction layer and the previously separated organic layer were transferred to a 12-liter, 3-neck round bottom flask fitted with a mechanical stirrer, thermometer, pH meter electrode and pressure equalizing addition funnel.

Equal volume amounts of water (1281 ml) and n-heptane (1281 ml) were added and the resulting mixture was cooled to about 0° C. to about 5° C. The cooling of the mixture minimized any side reaction likely to cause removal of the BOC group.

The mixture was then acidified with a mineral acid, an aqueous solution of 6 N hydrochloric acid. The acid solution (442 ml) was slowly added to the reaction mixture until the pH was about 1.3 to about 1.7. The 6 N HCl solution was prepared by adding concentrated HCl (12 N) slowly to an equal portion of water and allowing the solution to cool to room temperature before use. The acidified solution was stirred for about one hour at a temperature of about 0° C. to about 5° C.

The aqueous and organic layers were then separated. The organic layer was washed with water (640 ml) and again separated from the resulting water layer. The separated organic layer was heated to reflux (45°–55° C.).

n-Heptane (3843 ml) was added slowly to the refluxed organic layer over a period of 60 to 90 minutes. The n-heptane-containing solution was then cooled to about 30° C. to about 35° C.

A small amount (approximately 8 grams) of previously obtained BOC beta-benzyl-L-aspartic acid was added to the cooled n-heptane solution. Addition was continued until the solution appeared cloudy, indicating that crystallization had begun. Another addition of n-heptane (2562 ml) was made over a period of 45–60 minutes. The temperature of the solution was maintained at about 30° C. to about 35° C. This mixture was then stirred for about one hour.

The stirred mixture was thereafter distilled at 30° C. to about 40° C. at 15–20 inches Hg to a final pot volume of approximately 9000 ml. The pot volume before distillation was approximately 10,650 ml. Methylene chloride was removed during distillation.

n-Heptane (1650 ml) was added to the distillate and the resulting mixture was cooled to room temperature to complete the crystallization. A solid material, later identified as BOC-beta-benzyl-L-aspartic acid, was recovered from the solution by filtration. The solid material was transferred to a funnel for filtration and the flask was rinsed with n-heptane (500 ml). The filter cake was washed with fresh n-heptane (1500 ml), air dried for about 30 to about 45 minutes, then dried at room temperature under reduced pressure for about 24 hours.

The yield of BOC-beta-benzyl-L-aspartic acid was 782.1 g (94.5 percent). The melting point was found to be 101°–102° C.

EXAMPLE 2: BOC-Beta-Benzyl-L-Aspartic Acid Preparation

In a manner similar to Example 1, a three phase aqueous mixture of water, methylene chloride (769 ml), di-t-butyldicarbonate (635.13 g), and beta-benzyl-L-aspartic acid (571.81 g) is made.

An amount of triethylamine is then added as the organic base (512 ml). The triethylamine is added slowly in 15–20 ml aliquots, until the pH of the resulting mixture measures in the range of 8.0–8.5. The mixture is then heated to about 30° C. to about 40° C. The remaining triethylamine is thereafter added slowly while maintaining the pH of the mixture in the range of about 7.5 to about 9.

After all of the triethylamine is used, the produced mixture is stirred while the temperature is maintained between about 30° C. to about 40° C. for about 1 hour or until no solids are present in the reaction vessel.

Following the stir period, BOC-beta-benzyl-L-aspartic acid is recovered as a non-aqueous solution of its triethylamine salt or is extracted and crystallized as in Example 1 hereinabove.

The present invention has been described with respect to preferred embodiments. It will be apparent to those skilled in the art that modifications and/or variations of the disclosed compositions and methods can be made without departing from the scope of the invention set forth herein.

What is claimed is:

1. A method for producing a crystalline amino-blocked beta-benzyl-L-aspartic acid which comprises combining an oxycarbonyl compound providing an amino protecting group with beta-benzyl-L-aspartic acid and a tertiary amine organic base having a $pK_a$ value of about 9 to about 12 in the presence of water and a water-immiscible polar organic solvent, and at a pH value of about 7.5 to about 9, and maintaining the resulting combination of constituents for a time period sufficient to produce a non-aqueous solution of a salt of amino-blocked beta-benzyl-L-aspartic acid;

recovering said non-aqueous solution;

adding water and a water-insoluble, non-polar organic liquid phase modifier to said non-aqueous solution to produce a liquid having an aqueous phase and an organic liquid phase;

acidifying said liquid to a pH value of about 0.5 to about 2;

separating the organic liquid phase from the acidified liquid; and adding an additional amount of said organic liquid phase modifier to the separated organic liquid phase sufficient to induce crystallization of amino-blocked beta-benzyl-L-aspartic acid from said separated organic liquid phase.

2. The method in accordance with claim 1 wherein the additional amount of said organic liquid phase modifier is added stage-wise during crystallizaton.

3. The method of claim 1 wherein said oxycarbonyl compound is di-t-butyl-dicarbonate.

4. The method of claim 1 wherein said tertiary amine organic base is triethylamine.

5. The method of claim 1 wherein said polar organic solvent is methylene chloride.

6. The method of claim 1 wherein said organic liquid phase modifier is an aliphatic $C_5$ to $C_8$ hydrocarbon.

7. The method of claim 6 wherein said aliphatic $C_5$ to $C_8$ hydrocarbon is n-heptane.

8. The method of claim 1 wherein at least one seed crystal of said amino-blocked beta-benzyl-L-aspartic acid is added to said separated organic liquid phase.

9. A method of producing crystalline t-butyloxycarbonyl-beta-benzyl-L-aspartic acid which comprises:
 (a) combining methylene chloride with di-t-butyldicarbonate to produce a liquid admixture;
 (b) adding water to said admixture to produce a system containing an aqueous phase and an organic liquid phase;
 (c) adding beta-benzyl-L-aspartic acid to said system;
 (d) adding a mixture of triethylamine and methylene chloride to said system until a pH value for the system in the range of about 7.8 to about 8.5 is obtained;
 (e) separating said organic liquid phase from said aqueous phase;
 (f) adding water and n-heptane to said separated organic liquid phase and cooling the mixture thereof to a temperature of about 0° C. to about 5° C. to obtain, once more, an aqueous phase and an organic liquid phase;
 (g) acidifying said cooled mixture to a pH value of about 1.3 and about 1.7 and separating the organic liquid phase from the aqueous phase in the acidified, cooled mixture;
 (h) adding additional n-heptane and at least one seed crystal of t-butyloxycarbonyl-beta-benzyl-L-aspartic acid to said last-named organic liquid phase;
 (i) distilling said last-named organic liquid phase at a reduced pressure;
 (j) adding more n-heptane to said organic liquid phase and cooling it to at least about room temperature; and
 (k) recovering crystalline t-butyloxycarbonylbeta-benzyl-aspartic acid as a product of the process.

10. The method of claim 9 wherein the reduced pressure during distillation is about 15 to about 25 inches of mercury.

11. A method for producing an amine salt of amino-blocked beta-benzyl-L-aspartic acid in relatively pure form which comprises
 combining an oxycarbonyl compound providing an amino protecting group with beta-benzyl-L-aspartic acid and a tertiary amine organic base having a $pK_a$ value of about 9 to about 12 in the presence of water and a water-immiscible polar organic solvent, and at a pH value of about 7.5 to about 9, and maintaining the resulting combination of constituents for a time period sufficient to produce a non-aqueous solution of a salt of amino-blocked beta-benzyl-L-aspartic acid; and
 recovering said non-aqueous solution containing relatively pure amino-blocked beta-benzyl-L-aspartic acid as the corresponding amine salt.

12. The method of claim 11 wherein said non-aqueous solution is constituted by the amino-blocked beta-benzyl-L-aspartic acid as an amine salt, triethylamine and methylene chloride.

13. The method in accordance with claim 12 wherein the amino-blocked beta-benzyl-L-aspartic acid is BOC-β-benzyl-L-aspartic acid.

* * * * *